(12) United States Patent
Petersen et al.

(10) Patent No.: US 8,742,182 B2
(45) Date of Patent: *Jun. 3, 2014

(54) METHOD OF OPERATING A DISTILLATION COLUMN FOR PURIFYING 1,2-DICHLOROETHANE AND FOR COUPLED SODIUM HYDROXIDE SOLUTION EVAPORATIVE CONCENTRATION

(75) Inventors: Sven Petersen, Kelkheim (DE); Michael Benje, Darmstadt (DE); Peter Kammerhofer, Burglirchen (DE)

(73) Assignees: Uhde GmbH, Dortmund (DE); Vinnolit GmbH & Co. KG, Burgkirchen (DE)

( * ) Notice: Subject to any disclaimer, the term of this patent is extended or adjusted under 35 U.S.C. 154(b) by 1514 days.

This patent is subject to a terminal disclaimer.

(21) Appl. No.: 11/991,699

(22) PCT Filed: Sep. 7, 2006

(86) PCT No.: PCT/EP2006/008703
§ 371 (c)(1),
(2), (4) Date: Nov. 17, 2008

(87) PCT Pub. No.: WO2007/031223
PCT Pub. Date: Mar. 22, 2007

(65) Prior Publication Data
US 2009/0082602 A1    Mar. 26, 2009

(30) Foreign Application Priority Data

Sep. 15, 2005 (DE) .......................... 10 2005 044 177

(51) Int. Cl.
*C07C 17/00* (2006.01)
(52) U.S. Cl.
USPC ......................................................... 570/224
(58) Field of Classification Search
None
See application file for complete search history.

(56) References Cited

U.S. PATENT DOCUMENTS 6,191,329 B1 * 2/2001 Benje .............................. 570/243
7,182,840 B1 * 2/2007 Benje et al. ...................... 203/25

FOREIGN PATENT DOCUMENTS

DE          40 39 960 A1    9/1991
WO       WO 0134542 A2     3/2001

* cited by examiner

*Primary Examiner* — Clinton Brooks
(74) *Attorney, Agent, or Firm* — Marshall & Melhorn, LLC

(57) ABSTRACT

Process for operating a distillation column for the removal of water and lower-boiling components than 1,2-dichloroethane from 1,2-dichloroethane in which at least part of the heat from condensation of the aqueous vapors from the distillation column is used to concentrate caustic soda solution by evaporation; furthermore, at least part of the 1,2-dichloroethane formed when chlorine and ethylene react in a direct chlorination unit is used to heat said distillation column and can subsequently also be used as a heat transfer fluid to concentrate caustic soda solution by evaporation.

3 Claims, 1 Drawing Sheet

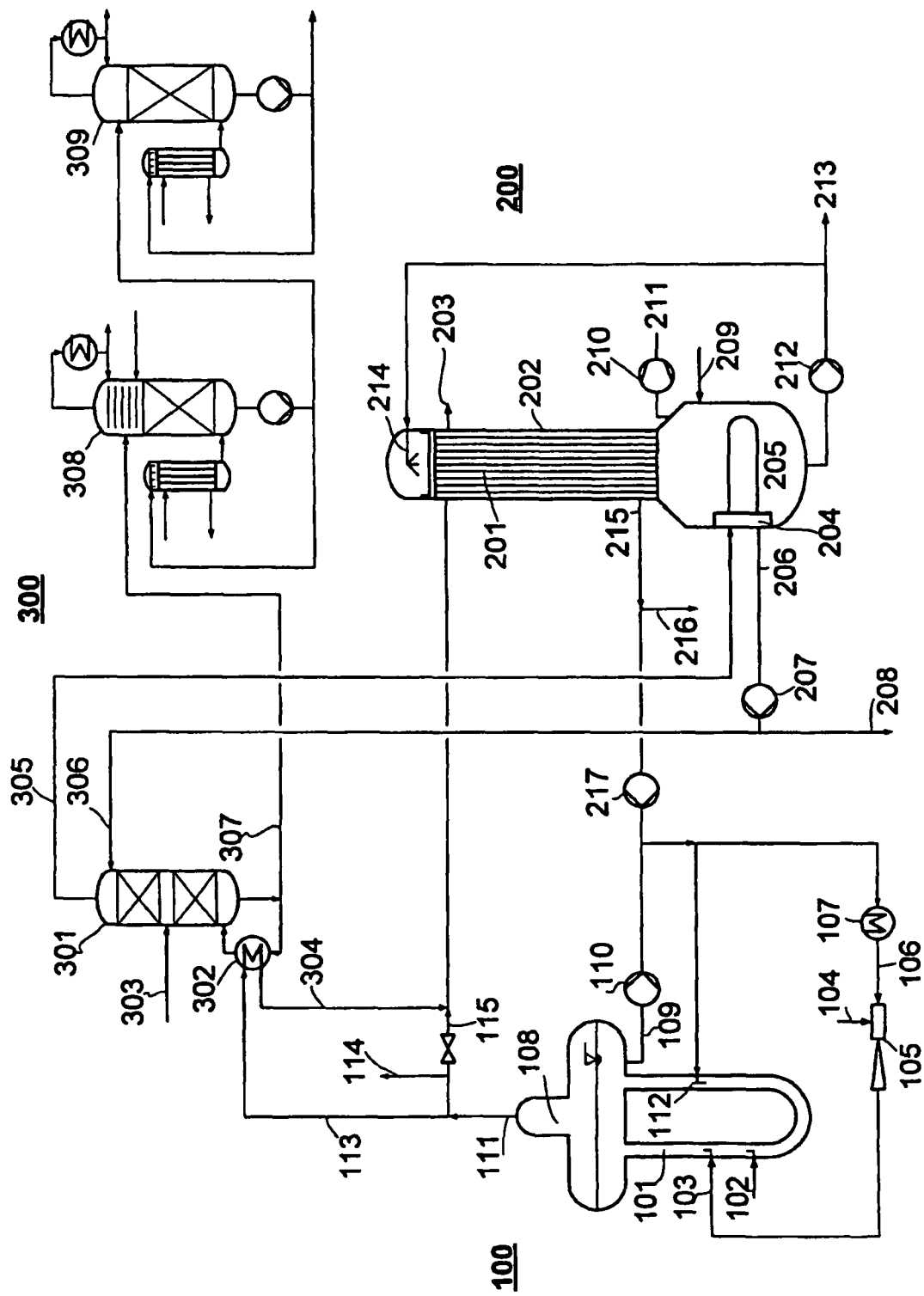

METHOD OF OPERATING A DISTILLATION COLUMN FOR PURIFYING 1,2-DICHLOROETHANE AND FOR COUPLED SODIUM HYDROXIDE SOLUTION EVAPORATIVE CONCENTRATION

BACKGROUND OF THE INVENTION

The process relates to a process for the production of 1,2-dichloroethane, hereinafter referred to as EDC. EDC is primarily used as an intermediate product in the production of monomer vinyl chloride, hereinafter referred to as VCM, which, in turn, is used to produce polyvinyl chloride (PVC). When EDC reacts to form VCM, hydrogen chloride (HCl) is obtained. Hence, EDC is preferably produced from ethylene ($C_2H_4$) and chlorine ($Cl_2$) in a manner such as to maintain a balance between the hydrogen chloride (HCl) produced and that consumed in the reactions, as shown in the following reaction equations:

$$Cl_2 + C_2H_4 \rightarrow C_2H_4Cl_2 \text{ (pure EDC)} + 218 \text{ kJ/Mol} \quad (1)$$

$$C_2H_4Cl_2 \text{ (cracked EDC)} \rightarrow C_2H_3Cl \text{ (VCM)} + HCl - 71 \text{ kJ/Mol} \quad (2)$$

$$C_2H_4 + 2HCl + \tfrac{1}{2}O_2 \rightarrow C_2H_4Cl_2 \text{ (raw EDC)} + H_2O + 238 \text{ kJ/Mol} \quad (3)$$

The process for the production of VCM with an adequate HCl balance, hereinafter referred to as "balanced VCM process", comprises:

a direct chlorination step, in which a portion of the required EDC is produced from ethylene ($C_2H_4$) and chlorine ($Cl_2$) and generated as pure EDC; utilising the heat of reaction produced in this direct chlorination step is a central aspect of the invention;

an oxychlorination step, in which the rest of the EDC is produced from ethylene ($C_2H_4$), hydrogen chloride (HCl) and oxygen ($O_2$), and generated as raw EDC;

a fractionating EDC purification step, in which the raw EDC, together with the recycle EDC returned from the VCM fractionation step, is freed from the by-products formed in the oxychlorination and EDC pyrolysis steps in order to obtain a feed EDC suitable for use in the EDC pyrolysis step;

an EDC pyrolysis step, in which the pure EDC is combined with the feed EDC and the resulting EDC mixture is thermally cracked; the cracked gas obtained consists of VCM, hydrogen chloride (HCl) and unreacted EDC as well as by-products;

a VCM fractionation step, in which the pure VCM desired as product is separated from the cracked gas, and the other main substances contained therein, namely hydrogen chloride (HCl) and unreacted EDC, are recovered separately as recyclables and returned to the balanced VCM process as reusable feed in the form of recycle HCl or recycle EDC.

The chlorine ($Cl_2$) required for the direct chlorination step is normally produced in a sodium chloride-(NaCl) electrolysis plant, with caustic soda (NaOH) with a concentration of about 33% yielded as co-product. Due to the high toxicity of the chlorine ($Cl_2$) produced, transportation over long distances is avoided where possible. Hence, the chlorine ($Cl_2$) required for the direct chlorination step is often produced in the vicinity of the direct chlorination unit.

It is commonly known that the minor constituents formed in the cracked gas during the EDC pyrolysis step reduce the purity of the VCM product. Removing these constituents in order to improve the purity of the VCM is costly. Hence, cracked EDC which has been largely freed from such impurities is used in the EDC pyrolysis step. Of the large number of techniques that exist for preventing or, if necessary, removing such detrimental by-products and/or constituents, reference is made in particular to patent specification WO 01/34542 A2, and especially to the state of the art described therein. This shows that the heat released when ethylene ($C_2H_4$) and chlorine ($Cl_2$) react to form liquid EDC during the direct chlorination process is sufficient to operate the purification columns for the EDC produced in the "balanced VCM process".

However, a disadvantage of the process described therein is that the heat of reaction used to heat the purification columns requires the withdrawal of a corresponding quantity of heat in order to condense the vapours. This is done in accordance with a conventional state-of-the art technique, usually by means of cooling water, which must be provided in large quantities. However, even if the purification columns are not operated by the off-heat arising from the heat of reaction from the direct chlorination unit, cooling water must be provided in large quantities in order to condense the vapours from the purification columns.

BRIEF SUMMARY OF THE INVENTION

Hence, the purpose of the invention is to further optimise utilisation of the off-heat from the "balanced VCM process" and to substantially reduce the cooling water requirement.

The invention achieves its purpose by utilising the heat from condensation of the vapours arising from the distillative separation of lower-boiling components than EDC at least in part to concentrate by means of evaporation the caustic soda solution produced as co-product during the production of chlorine. This type of distillation column, known as a lights column, is a normal component of the "balanced VCM process". In this process the lower-boiling components to be separated are mainly reaction water fed to the lights column during oxychlorination, which then needs to be separated from the EDC, and organic lower-boiling components than EDC.

In remote areas, in particular, the costs of transporting the caustic soda solution (NaOH) obtained in the NaCl electrolysis plant are an important factor. These costs can be substantially reduced if the approx. 33% solution obtained is concentrated to 50% solution by evaporation. Plants for evaporating caustic soda solution (NaOH) accordingly can, for example, be operated under vacuum at an absolute pressure of 133 mbar and a temperature of 60° C. Even in cases where the EDC production unit and the NaCl electrolysis plant are not located next to each other, it is worth transporting the 33% caustic soda solution obtained to the EDC production unit first in order to concentrate the NaOH solution in a vacuum evaporation unit operated by EDC. Of course, the solution may be evaporated to concentrations other than 50% depending on customer requirements and the off-heat produced.

In an embodiment of the invention, at least part of the EDC formed when chlorine and ethylene react in a direct chlorination unit is used to heat the distillation column for the removal of water and lower-boiling components than EDC.

In a further embodiment of the invention, at least part of this EDC which was used to heat the distillation column for the removal of water and lower-boiling components than EDC can then also be used as a heat transfer fluid to concentrate caustic soda solution by evaporation. This is possible because the temperature level to which the lights column is heated is higher than that of the caustic soda evaporation unit and it is therefore possible to further reduce the temperature of the EDC vapours condensed during heating of the distillation column by releasing energy in the caustic soda evaporation unit.

The process equipment and apparatus used to transfer the condensation energy consist of the familiar balanced VCM process equipment and the apparatus for concentrating the caustic soda solution (NaOH) by evaporation. The latter mainly refers to a vertical shell-and-tube heat exchanger with two fixed tube sheets and an NaOH sump, in which the caustic soda solution (NaOH) flows down through the tubes and the low-boiling vapours outside the tubes. The heat transfer between the shell and tube side takes place in a co-current flow. The vapours introduced into the top of the tube bundle condensate and can be withdrawn as liquid at the bottom.

Another appropriate method of heat transfer is by means of a heat exchanger tube bundle inserted in the caustic soda sump or by a reboiler, e.g. of the kettle type, positioned outside the caustic soda sump.

All of the methods described above can also be used additively or in combination. If the process is to be used in combination with other processes which also include caustic soda evaporation and in so doing different vapours are to be used at the same time, the tube bundle can be partitioned horizontally. Of course, it must be ensured that the individual streams of vapours from different distillation columns do not get mixed with each other.

BRIEF DESCRIPTION OF THE DRAWING

In accordance with the principle described in WO 01/34542 A2, FIG. 1 shows a simplified process flow diagram illustrating an EDC purification unit configuration (300) with a direct chlorination unit (100) and a caustic soda evaporation unit (200) in a plant based on the "balanced VCM process", where
the vapours from the lights column (301) of the EDC purification unit (300) are condensed in a caustic soda evaporation unit (200) in accordance with the main claim,
the lights column (301) is heated by the EDC vapours from the direct chlorination unit (100) in accordance with claim 2, and
after heating the lights column (301), the condensate from the EDC vapours is used in the caustic soda evaporation unit (200) in accordance with claim 3.

DETAILED DESCRIPTION OF THE INVENTION

The direct chlorination unit (100) consists of a liquid-filled loop (101), an ethylene feeder (102), a feeder for chlorine which has been dissolved in EDC (103)—with the pre-dissolving of the chlorine gas (104) in liquid EDC (106) in an injector (105) and prior to this the cooling of the liquid EDC to a low temperature in the EDC cooler (107) in order to improve solubility—and in addition an evaporation drum (108), a discharge device for liquid EDC (109) with an EDC circulation pump (110), a discharge device for vaporous EDC (111) and a feed point for recycle EDC (112)—although, for practical reasons, there may be more than one of each of the feed points and discharge devices. In the liquid-filled loop (101) chlorine reacts with ethylene to form boiling EDC, which evaporates in the evaporation drum (108) together with the unreacted feedstocks and minor inert constituent gases.

Part of the vaporous EDC (113) is fed to the sump reboiler (302) of the lights column (301). The portion of the total vaporous EDC (113) withdrawn from the direct chlorination unit which is to be fed to this reboiler depends on the mode of operation employed by the lights column (301), in particular on the respective water content in the raw EDC (303) and the specifications relating to separation purity, and normally amounts to around a fifth of a third thereof. The remaining vaporous EDC (114) is usually used elsewhere in the balanced VCM process or may also be used to concentrate the caustic soda solution by evaporation.

The temperature of the sump in the lights column (301) is typically about 115° C. while the vaporous EDC can be withdrawn from the direct chlorination unit (100) at about 120-125° C. On account of this slight difference in temperature, it is hardly possible to remove in this way any more off-heat from the EDC beyond the condensation itself to operate the lights column (301), which is why the EDC condensate (304), which still contains vaporous EDC and inert gas components, is discharged from the sump reboiler (302) as a multi-phase mixture at a temperature of approximately 120° C.

The EDC condensate (304) is sent to the caustic soda evaporation unit (200), if necessary after being mixed with vaporous EDC (115). In the evaporation unit, which is designed as a vertical tube bundle with an enlarged sump, it is directed to the shell side (201) of the shell-and-tube heat exchanger (202) while a falling film evaporation of the caustic soda solution takes place on the tube side at about 60° C. Non-condensibles are discharged via an inert gas outlet (203). Here, suitable technical measures must be taken to prevent the formation of explosive gas mixtures on the shell side (201) of the shell-and-tube heat exchanger (202). Such measures are familiar to a person skilled in the art and not an object of the present invention.

The light vapour (305) from the lights column (301) is also sent to the caustic soda evaporation unit (200), where it is condensed in the immersion cooler (204) installed in the sump (205) of the caustic soda evaporation unit (200). Part of the light condensate obtained (206) is returned to the head of the lights column (301) as light reflux (306) by the condensate pump (207) and part is discharged as waste water (208). The big temperature difference between the caustic soda evaporation unit (200) at approximately 60° C. and the head of the lights column (301) at approximately 90° C. makes a compact design possible.

The 33% caustic soda solution (209) is fed to the sump (205) of the caustic soda evaporation unit (200) and concentrated under vacuum to approximately 50%. The pressure is maintained by means of a vacuum pump (210), which discharges the water vapour as it is liberated (211). A caustic soda pump (212) discharges part of the concentrated caustic soda solution as product NaOH (213) and pumps the remaining part to the caustic soda distributor (214), which distributes the caustic soda solution to be concentrated to the tube side of the shell-and-tube heat exchanger (202).

The EDC-containing bottoms (307) of the lights column (301) are sent to the heavies column (308). In this column and in the subsequent vacuum column (309) they are purified further in the familiar way. The reaction heat from the production of EDC can also be used beneficially to heat these columns, but this is not an object of the present invention.

Product EDC (216) is tapped from the pure EDC (215) withdrawn from the shell side (201) of the shell and tube heat exchanger (202); the remaining pure EDC is pumped to the loop in the direct chlorination unit (100) by means of an EDC pump (217) and combined with the liquid EDC (109).

Here, the circuit for the vapours from the direct chlorination unit (100) and the lights column (301) is shown by way of example only. It would also be possible to use an external reboiler in the caustic soda evaporation unit (200) or to partition the shell side (201). Here, there is some freedom with respect to which vapour can be fed to which component as a heating agent—something which a person skilled in the art would need to optimise to enhance efficiency in each particular case while of course taking care to ensure that the different quality EDC streams do not get mixed with each other.

A typical example is shown below on the basis of a calculation using simulation: it is based on a plant with a capacity of 400 000 tpy of EDC. With this size plant a thermal output of approximately 3.9 MW can be achieved in the lights column at a head pressure of 1.15 bar abs. and a temperature of approximately 91° C. for use in the caustic soda evaporation unit, allowing approximately 6.8 t/h of caustic soda solution (calculated as 100%) to be concentrated from 33 to 50 wt. %. 5.2 MW from the direct chlorination unit are introduced into the sump reboiler in order to operate the lights column, amounting to 30% of the total reaction heat.

LIST OF REFERENCE NUMBERS USED

100 Direct chlorination unit
101 Liquid-filled loop
102 Ethylene feeder
103 Dissolved chlorine
104 Chlorine gas
105 Injector
106 Liquid EDC
107 EDC cooler
108 Evaporation drum
109 Liquid EDC
110 EDC circulation pump
111 Vaporous EDC
112 Recycle EDC
113 Vaporous EDC
114 Vaporous EDC
115 Vaporous EDC
200 Caustic soda evaporation unit
201 Shell side
202 Shell-and-tube heat exchanger
203 Inert gas outlet
204 Immersion cooler
205 Sump
206 Light condensate
207 Condensate pump
208 Waste water
209 33% caustic soda solution
210 Vacuum pump
211 Water vapour
212 Caustic soda pump
213 Product NaOH
214 Caustic soda distributor
215 Pure EDC
216 Product EDC
217 EDC pump
300 EDC purification unit
301 Lights column
302 Sump reboiler
303 Raw EDC
304 EDC condensate
305 Light vapour
306 Light reflux
307 Bottoms
308 Heavies column
309 Vacuum column

The invention claimed is:

1. A process for the production of 1,2-dichloroethane, the process comprising:
 a direct chlorination step, wherein ethylene and chlorine are combined to form 1,2-dichloroethane and heat is generated by the process;
 an oxychlorination step wherein additional 1,2-dichloroethane is produced from ethylene, hydrogen chloride and oxygen;
 a fractioning purification step wherein the 1,2-dichloroethane is freed from byproducts; and
 a pyrolysis step wherein 1,2-dichloroethane is thermally cracked, the cracked gas comprising monomer vinyl chloride, hydrogen chloride, unreacted 1,2-dichloroethane and byproducts, wherein the unreacted 1,2-dichloroethane is returned to the fractioning purification step; wherein
 the heat from the direct chlorination step is used for the removal of water and lower-boiling components than 1,2-dichloroethane, wherein at least part of the heat from condensation of the water vapor from the distillation column is used to concentrate caustic soda by evaporation.

2. The method according to claim 1, wherein at least part of the 1,2-dichloroethane formed when chlorine and ethylene react in a direct chlorination unit is used to heat the distillation column for the removal of water and lower-boiling components than 1,2-dichloroethane from 1,2-dichloroethane.

3. The method according to claim 2, wherein at least part of the 1,2-dichloroethane which was used to heat the distillation column for the removal of water and lower-boiling components than 1,2-dichloroethane is subsequently used as a heat transfer fluid to concentrate caustic soda solution by evaporation.

* * * * *